United States Patent [19]

Hsiao et al.

[11] Patent Number: 4,845,229
[45] Date of Patent: Jul. 4, 1989

[54] PROCESS FOR INTERMEDIATES TO 1-CARBAPENEMS AND 1-CARBACEPHEMS

[75] Inventors: Chi-nung W. Hsiao; Marvin J. Miller, both of South Bend, Ind.

[73] Assignee: University of Notre Dame du Lac, Notre Dame, Ind.

[21] Appl. No.: 160,801

[22] Filed: Feb. 26, 1988

Related U.S. Application Data

[62] Division of Ser. No. 780,101, Sep. 25, 1985, Pat. No. 4,745,201.

[51] Int. Cl.[4] ............................................. C07D 277/06
[52] U.S. Cl. ..................................................... 548/110
[58] Field of Search ......................................... 548/110

[56] References Cited

PUBLICATIONS

Evans, D. A., et al., "Enantioselective Aldol Condensation. Erythro–Selective Chiral Aldol Condensations via Boron Enolates", *J. Am. Chem. Soc.*, 1981, 103, 2127.

Wentrup, C., et al., "A Stereocontrolled Synthesis of (+)-Thienamycin", *J. Am. Chem. Soc.*, 1980, 102, 6161–6163.

Salzmann, T. N., et al., "Total Synthesis of (−)-Homothienamycin", *Tetrahedron Letters*, vol. 21, pp. 1193–1196, 1980.

Soai, K., et al., "Synthesis of 1,3-Thizolidine-2-Thione and (4R)–Methoxycarbonyl-1,3-Thiazolidine-2-Thione . . . ", *Heterocycles*, vol. 22, No. 12, 1984, 2827.

Nagao, Y., et al., *Tetrahedron Letters*, vol. 23, No. 2, pp. 201–204, 1984.

Jung, M., et al., *Tetrahedron Letters*, vol. 26, No. 8, pp. 977–980, 1985.

*Primary Examiner*—Nicky Chan
*Attorney, Agent, or Firm*—William B. Scanlon; Leroy Whitaker

[57] ABSTRACT

A stereoselective process for chiral intermediates to 1-carbapenem and 1-carbacephalosporins is provided comprising the use of an N-acyl-(4R)-substituted-1,3-thiazolidine-2-thione as a chiral auxiliary in boron enolate mediated aldol condensation with a protected-$\beta$-keto ester aldehyde. E.g., benzyl 3,3-(ethylenedioxy)-4-formylbutyrate is condensed with the boron enolate formed with n-butyryl (4R)-methoxycarbonyl-1,3-thiazolidine-2-thione to provide benzyl 3,3-ethylenedioxy-(5R)-hydroxy-6-[(4R)-methoxycarbonyl-1,3-thiazolidine-2-thione-3-ylcarbonyl]octanoate. Displacement of the thiazolidine-2-thione chiral auxiliary moiety with an O-alkyl, O-acyl or O-aralkyl hydroxyamine provides the corresponding chiral intermediate as the hydroxamate.

5 Claims, No Drawings

PROCESS FOR INTERMEDIATES TO 1-CARBAPENEMS AND 1-CARBACEPHEMS

This application is a division of application Seer. No. 06/780,101, filed 9-25-85, now U.S. Pat. No. 4,745,201.

BACKGROUND OF THE INVENTION

This invention relates to a stereoselective process for the preparation of chiral intermediates useful in the preparation of 1-carbapenem and 1-carbacephem antibiotics.

The non-classical β-lactam antibiotics such as the 1-carbapenems and 1-carbacephems are the subject of extensive study. Since these structures have not been obtained from natural sources, eg. as microbial metabolites, considerable effort is directed to asymmetric processes for their preparation in the desired stereochemical form.

SUMMARY

An N-acyl-(4R)-substituted-1,3-thiazolidine-2-thione chiral auxiliary is reacted with a di-($C_1$-$C_4$-alkyl)boryl trifluoromethanesulfonate and the boron enolate generated is reacted enantioselectively with a protected-β-keto ester aldehyde to provide the aldol condensation product

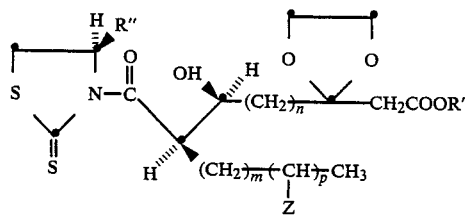

wherein R" is $C_1$-$C_4$ alkoxycarbonyl, benzyl, or substituted benzyl; R' is $C_1$-$C_4$ alkyl, or a carboxy-protecting group; Z is protected hydroxy; p is 0 or 1; m is 0, 1 or 2; and n is 1 or 2. The chiral auxiliary is easily displaced at room temperature with an O-alkyl, O-acyl, or O-aralkyl hydroxyamine $RONH_2$ to the corresponding β-hydroxy hydroxamate shown by the following partial formula

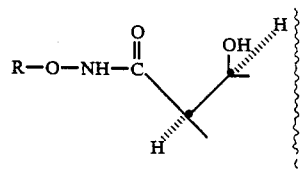

The chiral intermediates thus provided are cyclized to 3,4-disubstituted azetidinones with triphenylphosphine-diisopropyl azodicarboxylate or diethyl azodicarboxylate. Alternatively, the β-hydroxy group of the hydroxamate can be converted to the corresponding mesylate and the latter cyclized to the acetidinone by the procedure of Jung, M., and Miller, M. J., *Tetrahedron Letters*, 1985, 977. The azetidinones can be converted by known methods and procedures to 1-carbapenems and 1-carbacephalosporin antibiotic substances of the correct stereochemistry.

DETAILED DESCRIPTION

The stereoselective process of this invention comprises the use of an N-acyl-1,3-thiazolidine-2-thione as a chiral auxiliary in a boron enolate mediated aldol type condensation with a protected β-keto aldehyde. In particular, the process provides chiral intermediates useful in the preparation of 1-carbapenem and 1-carbacephalosporin antibiotics having the desired stereochemistry. The chiral intermediates are represented by the following formula 1

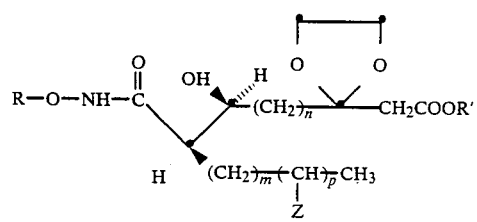

wherein R is $C_1$-$C_4$ alkyl, $C_1$-$C_4$ alkanoyl, benzyl, or substituted benzyl; R' is $C_1$-$C_4$ alkyl or a carboxy-protecting group; Z is protected hydroxy; n is 1 or 2; m is 0, 1 or 2; and p is 0 or 1.

According to the process, an N-acyl-1,3-thiazolidine-2-thione represented by the formula 2

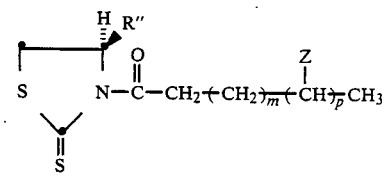

wherein R" is $C_1$-$C_4$ alkoxycarbonyl, benzyl, or substituted benzyl; and m, p, and Z are as defined above; is mixed with an inert solvent at a temperature between about −20° C. and about 15° C. with a di-($C_1$-$C_4$ alkyl)-boryl trifluoromethanesulfonate to form a boron enolate represented by the formula

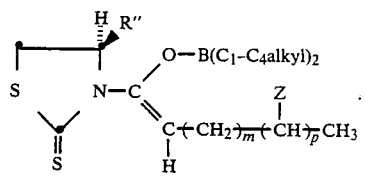

The boron enolate derivative is allowed to react at a temperature between about −90° C. and about −40° C. with the protected β-keto ester aldehyde represented by the formula 3

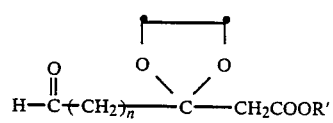

wherein n and R' have the same meanings as defined for formula 1, to form the condensation product represented by the formula 4

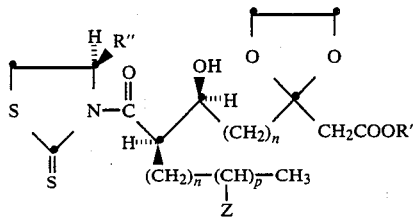

wherein R', R'', Z, n, m, and p have the same meanings as defined above.

The condensation product 4 is then allowed to react in an inert solvent with an O-alkyl, O-acyl or O-aralkyl hydroxamate R—O—NH$_2$ to effect displacement of the thiazolidine-2-thione chiral auxiliary and form the chiral intermdiate represented by the formula 1.

The N-acyl-1,3-thiazolidine-2-thione represented by the formula 2 is obtained by known methods via N-acylation of 1,3-thiazolidine-2-thione, eg. with an acyl halide represented by the formula

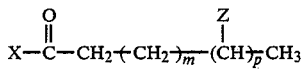

wherein X is chloro or bromo. For example, (4R)-methoxycarbonyl-1,3-thiazolidine-2-thione is N-acylated in methylene chloride with butyryl chloride (m=1, p=0) in the cold (ca −40° C.) in the presence of a hydrogen halide acceptor such as pyridine to form N-butyryl-(4R)-methoxycarbonyl-1,3-thiazolidine-2-thione.

The (4R)-1,3-thiazolidine-2-thione chiral auxiliary is obtaned by the method described by Nagao, Y., et al., *J. Am. Chem. Soc.* 1982, 104, 2079, or by the method described by Soai, K., Ishizaki, M., *Heterocycles,* 1984, 22, 2827.

The terms employed in defining the N-acylthiazolidine-2-thione, 2, have the following meanings. $C_1$–$C_4$ Alkoxycarbonyl refers to methoxycarbonyl, ethoxycarbonyl, n-propoxycarbonyl, iso-propoxycarbonyl, n-butoxycarbonyl, t-butoxycarbonyl, and sec-butoxycarbonyl. Substituted benzyl refers to the benzyl group substituted on the phenyl ring by one or two of the same or different groups of $C_1$–$C_4$ alkyl, $C_1$–$C_4$ alkoxy, 3,4-methylenedioxy, halogen, and nitro. Examples of such substituted benzyl groups are 4-methylbenzyl, 3,4-dimethylbenzyl, 4-t-butylbenzyl, 4-methoxybenzyl, 4-chlorobenzyl, 4-bromobenzyl, 3-chloro-4-methylbenzyl, 4-nitrobenzyl, and like groups. Protected hydroxy (Z) refers to a conventional hydroxy-protecting group capable of remaining intact under the conditions of the process. Examples of such protecting groups are tetrahydropyranyl, benzyl, substituted benzyl, e.g. p-methoxybenzyl and 4-methylbenzyl, trityl, allyl, and trialkylsilyl groups, e.g. trimethylsilyl and t-butyldimethylsilyl; the ketal formed with methylvinyl ether and the hydroxy group, the ketal formed with tetrahydro-4H-pyran-4-one, and like protecting groups.

The term carboxy-protecting group, R', refers to conventional carboxy-protecting ester groups such as the substituted alkyl groups, e.g. the haloalkyl groups, 2,2,2-trichloroethyl, 2,2,2-tribromoethyl, 2-iodoethyl, and the like; allyl, t-butyl, benzyl and substituted benzyl groups, e.g. 4-nitrobenzyl, 4-methoxybenzyl, 2,4-dimethylbenzyl, 4-chlorobenzyl, and the like; the diphenylmethyl and substituted diphenylmethyl groups such as 4-methoxydiphenylmethyl and 4,4'-dimethoxydiphenylmethyl; phenacyl, chlorophenacyl, and like ester groups.

Examples of N-acyl-1,3-thiazolidine-2-thiones which can be used in the process are N-propionyl-(4R)-methoxycarbonyl-1,3-thiazolidine-2-thione, N-butyryl-(4R)benzyl-1,3-thiazolidine-2-thione, N-valeryl-(4R)-t-butoxycarbonyl-1,3-thiazolidine-2-thione, N-($\beta$-benzyloxybutyryl)-(4R)-4-methylbenzyl-1,3-thiazolidine-2-thione, N-($\delta$-benzyloxy-n-valeryl)-(4R)-ethoxycarbonyl-1,3-thiazolidine-2-thione, and like N-acyl-thiazolidines.

Initially in the process, the N-acylthiazolidine 2 is converted to the boron enolate formed with a di-($C_1$–$C_4$ alkyl)boryl trifluoromethanesulfonate. The enolate formation occurs readily in the cold in the presence of a tertiary amine, preferably a hindered tertiary amine. Solvents which can be used are the halogenated hydrocarbons such as methylene chloride, mono-, di-, or trichloroethane, tetrahydrofuran, dioxane, or diethyl ether.

The formation of the enolate can be carried out at a temperature between about −20° C. and about 15° C., preferably about 0° C.

Amines which can be used are tri-n-butylamine, di(n-butyl)ethylamine, diisopropylethylamine, tri-n-propylamine, benzyl-di-(n-butyl)amine, t-butyl-diethylamine, and like tertiary amines.

A preferred boryl triflate for use in the process is di-(n-butyl)boryl trifluoromethanesulfonate.

The boron enolate derivative is formed in solution as evidenced by the development a yellowish solution. The solution of the enolate is cooled to a temperature between about −90° C. and about −40° C., preferably to about −80° C. to about −60° C., and the protected-$\beta$-keto ester aldehyde 3 is added. For best results in the process, at least the stoichiometric amount of the aldehyde, or preferably a slight excess, is added. The reaction mixture is agitated by stirring or shaking in the cold for about 30 minutes and is then allowed to warm to room temperature.

The condensation proceeds rapidly and is usually complete in less than an hour in the cold. If desired, the reaction mixture may be assayed for completeness by thin layer chromatography.

The condensation product 4 may be isolated, if desired, the product purified by chromatography over silica gel, and used in the next step of the process. Alternatively, the pH of the reaction mixture can be adjusted to about neutrality with a buffer, e.g. pH 7 phosphate buffer, the organic phase containing the product separated and filtered, if necessary, and the hydroxamate R—O—NH$_2$ added to the solution to form 1. The hydroxamate, e.g. O-benzyl hydroxyamine, is preferably added in an amount in excess of the stoichiometric amount and generally a 3–5 molar excess is used. The reaction proceeds at a convenient rate at or about room temperature with agitation.

The hydroxamate, R—ONH$_2$, used in the formation of 1 is prepared by known methods. Examples of hydroxamates when R is $C_1$–$C_4$ alkyl are methoxyamine, ethoxyamine, isopropoxyamine and t-butoxyamine; when R is benzyl or substituted benzyl examples are benzyloxyamine, 4-methylbenzyloxyamine, 4-methoxybenzyloxyamine, and 4-chlorobenzyloxyamine, and when R is $C_1$–$C_4$ alkanoyl examples includes acetoxyamine, propionoxyamine, pivaloyloxyamine, and butyryloxyamine.

Preferred hydroxamates are represented by RONH₂ where R is benzyl or acetoxy.

The formation of 1 in the process results from the ready displacement of the 1,3-thiazolidine-2-thione chiral auxiliary which can be recovered in high yields and reused in the process.

The intermediate 4 can be isolated and purified by chromatography prior to conversion to 1 with the hydroxamate RONH₂. Generally, chromatography over silica gel is satisfactory for purification.

In an example of the process, (4R)-methoxycarboxyl-1,3-thiazolidine-2-thione is acylated with butyryl chloride and the N-butyryl product converted to the boron enolate with di-(n-butyl)boryl trifluoromethanesulfonate. The enolate is condensed at −78° C. with methyl 3,3-(ethylenedioxy)-4-formylbutyrate in the presence of diisopropylethylamine to form 4 wherein R″ is methoxycarbonyl; m and n are 1; p is 0; and R′ is methyl.

The condensation product is then reacted with O-benzylhydroxylamine to provide 1 represented by the formula

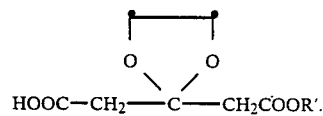

The carboxy group of the half ester is converted to the acid halide, e.g. with oxalyl chloride, and the acid chloride is reduced to the aldehyde 3 (n=1) with bis(triphenylphosphine) copper(I)tetrahydroborate in acetone.

The aldehyde 3 (n=2) is obtained with 3-oxoadipic acid by following essentially the same sequence of reactions. Alternatively, 3,3-(ethylenedioxy)adipic acid is esterified with one equivalent of the alcohol R′OH and the desired mono ester is separated by HPLC from the diester and any undesired mono ester. The half ester is converted to the aldehyde 3 via the acid chloride as described above.

The chiral products of the process represented by the formula 1 are useful as intermediates for 1-carbapenems and 1-carbacephalosporins. For example, the 1-car-

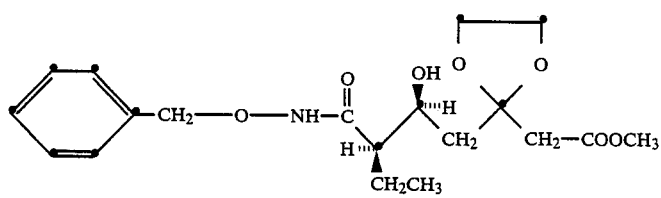

The protected-β-keto ester aldehydes represented by the formula 3 are prepared by known methods. Examples of these aldehydes are methyl 3,3-(ethylenedioxy)-4-formylbutyrate, benzyl 3,3-(ethylenedioxy)-4-formylbutyrate, ethyl 3,3-(ethylenedioxy)-5-formylvalerate, and 4-methoxybenzyl 3,3-(ethylenedioxy)-4-formyl valerate.

The aldehydes represented by formula 3 when n is 1 are obtained as follows: dimethyl 1,3-acetonedicarboxylate is converted to the cyclic ketal with ethylene glycol and toluenesulfonic acid. The ketal diester is saponified to the ketal diacid which is cyclized with a dehydrating agent to the cyclic glutaric anhydride represented by the formula

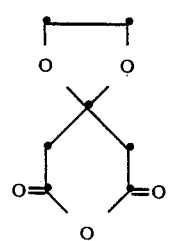

Dicyclohexylcarbodiimide or other suitable diimide is useful in forming the cyclic anhydride. The anhydride is reacted with the alcohol R′OH, wherein R′ has the same meanings as defined above, to form the half ester represented by the formula bapenem kown as PS-5 and represented by the formula

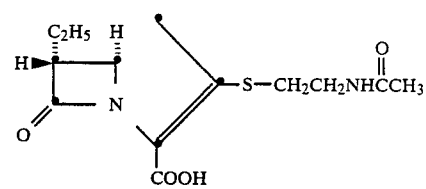

can be prepared with 1 wherein m and n are 1 and p is 0. The 1-carbacephalosporin represented by the formula below can likewise be prepared with 1.

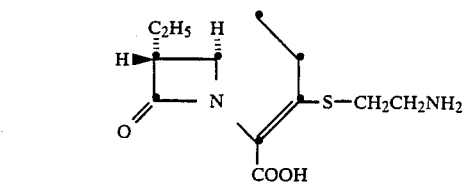

In converting the compound 1 to a 1-carbapenem or 1-carbacephalosporin, 1 is first converted to a substituted β-lactam represented by the formula

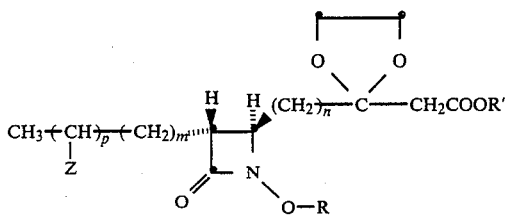

The formation of the β-lactam ring is carried out by reacting the β-hydroxy hydroxamate 1 in an inert solvent such as THF at about room temperature with about an equivalent amount of triphenylphosphine and a dialkyl azodicarboxylate such as diisopropyl azodicarboxylate. The cyclization is according to the procedure of Miller, M. J., et al., *J. Am. Chem. Soc.*, 1980, 102, 7026.

Alternatively, the β-hydroxy hydroxamate 1 can be converted to the mesylate ester with methanesulfonyl chloride at room temperature in the presence of pyridine. The β-methylate then undergoes cyclization to the azetidinone on treatment with potassium carbonate in methyl alcohol on standing or with stirring at room temperature.

The O-alkyl, O-acyl, O-benzyl, or O-substituted benzyl group attached to the ring nitrogen of the azetidinone is removed by known methods to form the corresponding N-hydroxyazetidinone represented by the formula

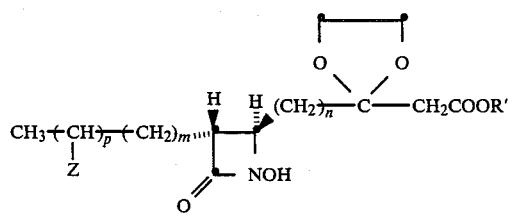

For example, the N-benzyloxyazetidinone is subjected to hydrogenolysis over palladium on carbon to remove the benzyl group and provide the corresponding N-hydroxyazetidinone. The N-acetoxy group is removed by hydrolysis. Reduction of the N-hydroxy compound with titanium trichloride according to Mattingly, P. G., and Miller, M. G., *J. Org. Chem.*, 45, 410 (1980) provides the corresponding NH azetidinone.

The ketal group in the 4-position substituent of the azetidinone is removed via treatment with perchloric acid, e.g. according to the procedure of Kametani, *J. Org. Chem.*, 1983, 47, 2328, to provide the β-keto ester compound represented by the formula A

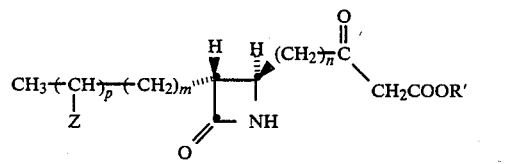

Diazo transfer with A and p-toluenesulfonyl azide provides the corresponding α-diazo-β-keto ester which, on cyclization with rhodium II acetate in chloroform, affords the bicyclic keto compound represented by the formula B

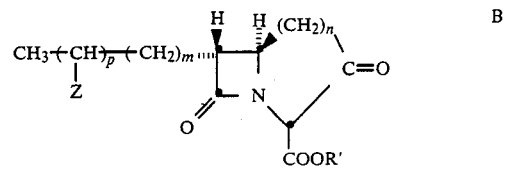

wherein n is 1 or 2. The keto group of B is converted to the 2-aminoethylthio derivative represented by the formula C

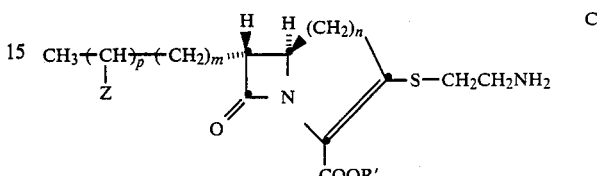

according to the procedure described by Salzmann, T. N., et al., *J. Am. Chem. Soc.*, 1980, 102, 6163–6165 and Salzmann, T. N., et al., *Tetrahedron Letters*, Vol. 21, pp. 1193–1196, 1980.

The protecting group of the protected-hydroxy group Z (when p=1) can be removed after formation of the bicyclic ring system or after formation of the final product. Depending of the nature of the carboxy-protecting group R' also present, both protecting groups may be removed under the same or different conditions. For example, when Z is a trityl group and R' is p-methoxybenzyl both groups may be removed under acidic conditions. The ester group is removed with trifluoroacetic acid and anisole and the trityl group with formic acid-hydrochloric acid.

Accordingly, when in the formula A n and m are 1 and p is 0, antibiotic PS-5 is obtained; when n is 1, m is 0, and p is 1, thienamycin is obtained; and when n is 2, m is 0, and p is 1, (−)homothienamycin is obtained.

Thus, the present invention provides a highly stereoselective process for the preparation of chiral intermediates useful in the preparation of antibiotic substances.

The process of this invention comprises the use of the (4R)-alkoxycarbonyl-1,3-thiazolidine-2-thione as a chiral auxiliary in combination with a boron enolate mediated aldol condensation. The chiral auxiliary is readily displaced under mild conditions following the stereoselective condensation. Further, the use of an oxidative work-up, such as with hydrogen peroxide, characteristically employed in previous boron enolate mediated aldol condensations is found to be unnecessary in the present process. Thus, the present process takes advantage of the combination of the 1,3-thiazolidine-2-thione as an easily displaceable chiral auxiliary with a boron enolate mediated aldo condensation to achieve high stereoselectivity in the preparation of chiral intermediates for antibiotics.

The followin Examples further illustrate the invention.

PREPARATION 1

Methyl 3,3-(ethylenedioxy)-4-formylbutyrate

A. Dimethyl 3,3-(ethylenedioxy)glutarate

A solution of dimethyl 1,3-acetonedicarboxylate (100 g; 0.574 mole; 1 eq.) ethylene glycol (320 ml; 10 eq.), toluene sulfonic acid monohydrate (20 g; 0.105 mole), methyl orthoformate (320 ml; 50 eq.) in 400 ml of tetrahydrofuran was heated at the reflux temperature for 40 hours. The colorless reaction mixture was cooled to room temperature and sodium bicarbonate (55 g; 0.6547 mole) was added, followed by the addition of 100 ml of water. The mixture was shaken thoroughly and distilled under reduced pressure to remove the tetrahydrofuran, excess methyl orthoformate, water and most of the ethylene glycol. The distillation was carried out in an oil bath at a temperature of about 115° C. at a reduced pressure of 2 torr. The temperatue reading at the top of the fractional column was not allowed to exceed 80° C.

Following the distillation, the residue was cooled, diluted with methylene chloride and treated with 100 ml of a saturated aqueous solution of sodium bicarbonate. The mixture was extracted three times with ethyl acetate, the organic layers combined, dried over magnesium sulfate, and concentrated under vacuum. The yellow oily residue was fractionally distilled under reduced pressure and the product, dimethyl 3,3-(ethylenedioxy)glutarate (87 g, 69.5% yield), was collected as a colorless oil at a temperature range of 120° C.-140° C./0.1 torr.

NMR ($\delta$, CHCl$_3$): 2.95 (s, 4), 3.70 (s, 6H) and 4.05 (s, 4H).

IR (cm$^{-1}$, neat): 1730, 1430, 1180, 1080 and 1020.

R$_f$(SiO$_2$, hexane/ethyl acetate; 1:1): 0.44.

B. Saponification of dimethyl 3,3-(ethylenedioxy)glutarate

To a solution of the dimethyl ester obtained as described above (20 g, 91.68 mmole, 1.0 eq.) in 250 ml of methanol was added at room temperature 1N sodium hydroxide solution, (140 ml, slightly in excess of 3.0 eq.). The reaction mixture was stirred at room temperature overnight, the methyl alcohol evaporated under vacuum, and the residue suspended in 250 ml of ethyl acetate. The suspension was acidified by the slow addition of 1N hydrochloric acid (approximately 295 ml of hydrochloric acid) and the acidified mixture was extracted with ethyl acetate (500 ml×4). The extract was dried over magnesium sulfate, filtered and evaporated under vacuum to yield 3,3-(ethylenedioxy)glutaric acid as a light yellow oil (13.016 g, 75% yield).

NMR ($\delta$, CHCl$_3$): 3.00 (s, 4H), 4.05 (s, 4H), and 11.15 (s, broad, 2H).

IR (cm$^{-1}$, neat): 2500-3500 (broad), 1710, 1050 and 740.

C. 3,3-(Ethylenedioxy)glutaric anhydride

To a solution of 3,3-(ethylenedioxy)glutaric acid (12.26 g, 64.50 mmole) in 300 ml of tetrahydrofuran maintained at 0° C. under nitrogen was added dropwise a solution of dicyclohexylcarbodiimide (13.60 g, 65.91 mmole) in 100 ml of tetrahydrofuran. The resulting suspension was stirred at room temperature overnight under nitrogen and the solvent was evaporated under vacuum. The residue was suspended in benzene, shaken thoroughly and filtered through silica gel packed in a column (10 cm long, SiO$_2$, 60-200 mesh, benzene). The filtrate was evaporated under vacuum to provide the anhydride (8.268 g, 75% yield) as a white crystalline solid melting at about 111° C. to about 112° C.

NMR ($\delta$, CHCl$_3$): 3.00 (s, 4H) and 4.05 (s, 4H).

D. 3,3-(Ethylenedioxy)glutaric acid mono methyl ester

A solution of the glutaric anhydride prepared as described in C. above (10 g, 58.14 mmole) in 150 ml of methyl alcohol was heated at the reflux temperature for 3 hours. A thin layer chromatogram (SiO$_2$, hexane/ethyl acetate, 1:1) indicated the total disappearance of the anhydride. The methyl alcohol was evaporated from the mixture by first evaporating the mixture in a rotary evaporator and then under high vacuum. The mono methyl ester was obtained as a nearly colorless, oily liquid (12.051 g, 100% yield, greater than 95% pure by NMR).

NMR ($\delta$, CHCl$_3$): 2.95 (s, 2H), 3.00 (s, 2H), 3.70 (s, 3H), 4.05 (s, 4H) and 10.50 (s, broad, 1H).

IR (cm$^{-1}$ neat): 2500-3500 (broad), 1720 (broad), 1200 and 1020.

E. 4-Carbomethoxy-3,3-(ethylenedioxy)butyryl chloride

To a solution of the mono methyl ester of 3,3-(ethylene-dioxy)glutaric acid (4.038 g, 19.794 mmole, 1.0 eq.) in 50 ml of dry benzene and maintained under nitrogen at room temperature was added oxalyl chloride (5.5 ml, slight excess over 3.0 eq.). The reaction mixture was stirred at room temperature overnight and the reaction mixture was evaporated under vacuum to remove benzene and excess oxalyl chloride. The acid chloride was obtained as a light yellow oil in better than 98% purity via NMR.

NMR ($\delta$, CHCl$_3$): 2.85 (s, 2H), 3.60 (s, 2H), 3.75 (s, 3H) and 4.05 (s, 4H).

F. Methyl 3,3-(ethylenedioxy)-4-formylbutyrate

The acid chloride prepared as described above in step E. was dissolved in 10 ml of acetone and the solution was added to a suspension of bis(triphenylphosphine)copper (I) tetrahydroborate (13 g, 21.56 mmole) in triphenylphosphine (10.5 g, 40.03 mmole) in 60 ml of acetone. The reaction mixture was stirred at room temperature for 1.5 hours and was filtered. The filtrate was concentrated under vacuum and the residue suspended in a mixture of hexane/ethyl acetate (4:1) and the suspension filtered. Following evaporation of the mixed solvents, the residue was resuspended in hexane/ethyl acetate as before and refiltered. The filtrate was evaporated under vacuum to yield a light yellow oil from which the title compound was separated by column chromatography over 60-200 mesh silica by using hexane/ethyl acetate, 4:1. The 4-formylbutyrate title compound was obtained as a colorless syrup (2.684 g, 72% yield) based on the glutaric acid half methyl ester.

NMR ($\delta$, CHCl$_3$): 2.80 (s, 2H), 3.00 (d, J=2.7 Hz, 2H), 3.75 (s, 3H), 4.10 (s, 4H) and 9.95 (t, J=2.7 Hz, 1H).

IR (cm$^{-1}$, neat): 1710.

R$_f$(SiO$_2$, hexane/ethyl acetate, 4:1): 0.14.

PREPARATION 2

Benzyl 3,3-(ethylenedioxy)-4-formylbutyrate

A. 3,3-(Ethylenedioxy)glutaric acid monobenzyl ester

To a solution of 3,3-(ethylenedioxy)glutaric anhydride prepared as described above in Preparation 1C. (2.046 g, 11.88 mmole) and benzyl alcohol (1.92 g, 17.75 mmole) in 30 ml of acetonitrile was added finely powdered potassium carbonate (5.0 g, 36.18 mmole). The suspension was stirred at room temperature overnight, the mixture evaporated under vacuum to remove acetonitrile and the semi-solid residue was suspended in diethyl ether, the suspension swirled for about 30 seconds, and the clear top ether solution was carefully decanted.

The ether washing process described above was repeated several times to insure the removal of excess benzyl alcohol. The washed residue was then suspended in ethyl acetate and 1N hydrochloric acid was added dropwise to the suspension until the aqueous layer turned acidic to pH paper. The acidic mixture was extracted with ethyl acetate (250 ml×4), was dried over magnesium sulfate, filtered and evaporated to yield the mono benzyl ester as a light yellow syrup (3.239 g, 97% yield).

NMR (δ, CHCl$_3$): 3.00 (s, 4H), 4.05 (s, 4H), 5.15 (s, 2H), 7.40 (s, 5H) and 10.75 (s broad, 1H).

IR (cm$^{-1}$, neat): 2500–3500 (broad), 1730, 1200, 1020, 730 and 680.

B. Benzyl 3,3-(ethylenedioxy)-4-formylbutyrate

By following the procedure employed in Preparation 1, E. and F., 3,3-(ethylenedioxy)glutaric acid mono benzyl ester prepared as described above in step A. (2.937 g, 10.48 mmole) was converted to the corresponding acid chloride with oxalyl chloride (3.0 ml, 34.39 mmole) in 30 ml of benzene. The acid chloride was reduced with bis(triphenylphosphine) copper (I) tetrahydroborate (6.32 g, 10.48 mmole) and triphenylphosphine (5.5 g, 20.97 mmole) in 50 ml of acetone. There was obtained 1.930 g, 70% yield of benzyl 3,3-(ethylenedioxy)-4-formylbutyrate, as a colorless syrup.

NMR (δ, CHCl$_3$): 2.85 (s, 2H), 3.00 (d, J=2.7 Hz, 2H), 4.05 (s, 4H), 5.20 (s, 2H), 7.45 (s, broad, 5H) and 9.85 (t, J=2.7 Hz, 1H).

IR (cm$^{-1}$, neat): 1720, 1225, 1025, 720 and 680.

R$_f$ (SiO$_2$, hexane/ethyl acetate, 9:1): 0.078, (SiO$_2$, benzene/diethyl ether, 9:1): 0.27.

PREPARATION 3

N-Butyryl-(4R)-methoxycarbonyl-1,3-thiazolidine-2-thione

To a suspension of (R)-cysteine (40.0 g, 0.330 mole) in 400 ml of methanol maintained under nitrogen at −78° C. was added thionyl chloride (28 ml, 0.384 mole). The cysteine slowly dissolved to form a clear solution. The solution was stirred overnight at room temperature and then evaporated under vacuum to yield (R)-cysteine methyl ester hydrochloride as a colorless, sticky syrup (57.0 g, 100% yield). The product solidified upon standing.

To a suspension of (R)-cysteine methyl ester hydrochloride prepared as described above (2.0 g, 11.66 mmole) in 20 ml of methylene chloride under nitrogen at room temperature was added triethylamine (2.0 ml, 14.35 mmole) and carbon disulfide (740 mμ, 12.30 mmoles). The suspension turned yellow immediately and after 10 minutes slowly faded to a light yellow solution. The reaction mixture was stirred overnight at room temperature and was then evaporated to yield (4R)-methoxycarbonyl-1,3-thiazolidine-2-thione as a white solid residue. The residue was suspended in ethyl acetate and filtered through a short (10 cm) column packed with 60–200 mesh silica gel. The column was eluted with ethyl acetate and the eluate was concentrated under vacuum, and the purified product separated from the concentrate by chromatography (silica, hexane/ethyl acetate, 4:1). There were obtained 1.796 g, 87% yield of (4R)-methoxycarbonyl-1,3-thiazolidine-2-thione as a light yellow oil.

NMR (δ, CHCl$_3$): 3.85 (d, J=7.5 Hz, 2H), 3.90 (s, 3H), 4.85 (t, J=7.5 Hz, 1H) and 7.8–8.3 (broad, 1H).

IR (cm$^{-1}$, neat): 3150–3350 (broad), 1750, 1465, 1220 and 1040.

R$_f$ (SiO$_2$, hexane/ethyl acetate, 1:1): 0.5.

[α]$_D^{20}$ = −64.497 (c=2.09, CHCl$_3$).

To a solution of (4R)-methoxycarbonyl-1,3-thiazolidine-2-thione (5.814 g, 32.847 mmole) in methylene chloride (100 ml) under nitrogen at −40° C. was added pyridine (2.66 ml, 32.844 mmole). The solution was stirred in the cold for 5 minutes and a solution of butyryl chloride (3.75 ml, 36.11 mmole) in 10 ml of methylene chloride was added dropwise. The reaction mixture was stirred at −40° C. for one hour and was then allowed to warm to room temperature over 30 minutes. After stirring overnight the reaction mixture was filtered through a 10 cm column packed with 60–200 mesh silica gel eluting with ethyl acetate. The filtrate was concentrated under vacuum and the concentrate chromatographed over 60–200 mesh silica gel using hexane/ethyl acetate, 4:1. The title compound (7.867 g, 97% yield) was obtained as a bright yellow oil.

NMR (δ, CHCl$_3$): 0.95 (t, J=7.5 Hz, 3H), 1.65 (quintet, J=7.5 Hz, 2H), 2.90–3.75 (m, 4H), 3.80 (s, 3H) and 5.65 (dd, J=7.5 Hz, J=7.5 Hz, 1H).

IR (cm$^{-1}$, neat): 1750, 1700, 1210, 1150 and 770.

[α]$_D^{20}$ = −123.529 (c=1.87, CHCl$_3$).

R$_f$ (SiO$_2$, hexane/ethyl acetate, 4:1): 0.297.

EXAMPLE 1

Condensation of N-Butyryl-(4R)-methoxycarbonyl-1,3-thiazolidine-2-thione and Methyl 3,3-(ethylenedioxy)-4-formylbutyrate To a solution of N-butyryl-(4R)-methoxycarbonyl-1,3-thiazolidine-2-thione (480 mg, 1.943 mmole) in 20 ml of methylene chloride cooled under nitrogen to 0° C. was added di-n-butylboryl trifluoromethanesulfonate (2.01 ml of a 1M solution in methylene chloride, 2.01 mmole). After stirring the solution for 5 minutes at 0° C., diisopropylethylamine (350 μl, 2.01 mmole) was added dropwise (1 drop per 5 seconds) with a micro syringe. The light yellow solution was stirred for another 30 minutes at 0° C. after addition of the amine. The solution was cooled to −78° C. and a solution of methyl 3,3-(ethylenedioxy)-4-formylbutyrate (368 mg, 1.960 mmole) in 3 ml of methylene chloride was added. The reaction mixture was stirred for 30 minutes at −78° C. and then was allowed to warm to 0° C. in about 20 minutes. A thin layer chromatogram of a small aliquot of the solution showed little thiazolidine-2-thione remaining. Excess pH 7 phosphate buffer (about 10 ml) was added and the mixture was stirred vigorously at 0° C. for 3 minutes. The yellow methylene chloride solution containing the product was separated from the aqueous layer and filtered through a silica gel column (10 cm long, 60–200 mesh, ethyl acetate). The filtrate was concentrated and the residue chromatographed over silica gel (hexane/ethyl acetate, 2:1) to yield methyl 3,3-ethylenedioxy-(5R)-hydroxy-6-[(4R)-methoxycarbonyl-1,3-thiazolidine-2-thione-3-ylcarbonyl]octanoate (654 mg, 77% yield) as a light yellow oil.

NMR (300 MHz, δ, CDCl$_3$): 0.99 (t, J=8 Hz, 3H), 1.64–1.80 (m, 1H), 1.86–2.00 (m, 1H), 2.05–2.22 (m, 2H), 2.75 (s, 2H), 3.25–3.36 (m, 2H), 3.69 (s, 3H), 3.82 (s, 3H), 4.03 (s, 4H), 4.20 (m, 1H), 4.87 (m, 1H), 5.67–5.70 (dd, J=3 Hz, J=8.5 Hz, 1H).

IR (cm$^{-1}$, neat): 3525, 1720 (broad).

$[\alpha]_D^{20} = -83.153$ (c=3.90, CHCl$_3$).

R$_f$(SiO$_2$, hexane/ethyl acetate, 1:1): 0.28

To a solution of the condensation product obtained as described above (122 mg, 0.280 mmole) in 1 ml of acetonitrile was added at room temperature O-benzylhydroxyamine (105 mg, 0.853 mmole). The mixture was stirred at room temperature for 6 hours and filtered through a silica gel column (10 cm, 60–200 mesh, ethyl acetate). The filtrate was concentrated under vacuum and the residue chromatographed over silica gel (hexane/ethyl acetate, 1:1), to yield (4R)methoxycarbonyl-1,3-thiazolidine-2-thione (45 mg, 915 yield) and methyl 3,3-ethylenedioxy-5R-hydroxy-6-(N-benzyloxy)aminocarbonyloctanoate (74 mg, 70% yield).

NMR (300 MHz, δ, CDCl$_3$): 0.95 (t, J=8 Hz, 3H), 1.64–1.80 (m, 1H), 1.86–2.00 (m, 1H), 2.05–2.20 (m, 3H), 2.70 (s, 2H), 3.65 (s, 3H), 3.72 (s, broad, 1H), 4.00 (s, broad, 4H), 4.85 (7.25–7.42 (m, 5H), and 8.84 (s, broad, 1H).

IR (cm$^{-1}$, neat): 3200–3600 (broad), 1730, 1660, 1200, 1010 and 730.

$[\alpha]_D^{20} = -8.78$ (c=3.70, CHCl$_3$).

R$_f$(SiO$_2$, hexane/ethyl acetate, 1:1): 0.166.

To a solution of the O-benzylhydroxamate prepared as described above (200 mg, 0.525 mmole) and triphenylphosphine (420 mg, 1.601 mmole) in 4 ml of dry tetrahydrofuran was added under nitrogen at room temperature diisopropyl azodicarboxylate (310 μl, 1.574 mmole). The reaction mixture was stirred at room temperature for 20 minutes at which time a thin layer chromatogram indicated that all of the starting material had reacted. The mixture was concentrated in vacuum and chromatographed over silica gel (230–400 mesh, hexane/ethyl acetate, 2:1) to yield 128 mg (67% yield) of N-benzyloxy-3-ethyl-4-(2,2-ethylenedioxy-3-methoxycarbonylprop-1-yl)azetidin-2-one represented by the formula

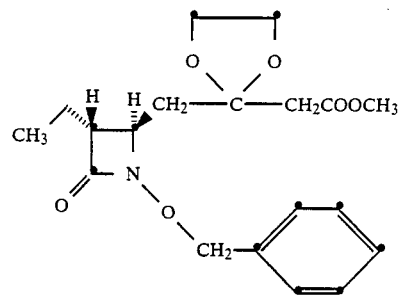

NMR (300 MHz, δ, CDCl$_3$): 0.96 (t, J=7.5 Hz, 3H), 1.54–1.68 (m, 2H), 2.00 (dd, J=8.7 Hz, J=14 Hz, 1H), 2.37 (dd, J=3.9 Hz, J=14 Hz, 1H), 2.58 (s, 2H), 2.61 (dt, J=1.8 Hz, J=6.6 Hz, 1H), 3.39 (ddd, J=1.8 Hz, J=3.9 Hz, J=8.7 Hz, 1H), 3.69 (s, 3H), 3.82–4.02 (m, 4H), 4.95 (s, 2H) and 7.30–7.50 (m, 5H).

$[\alpha]_D^{20} = +21.9$ (c=1.28, CHCl$_3$).

R$_f$(SiO$_2$, hexane/ethyl acetate, 2:1): 0.164.

We claim:

1. The boron enolate compound of the formula

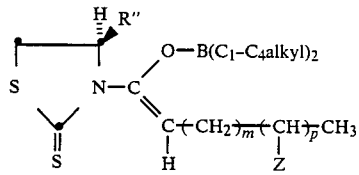

wherein R" is C$_1$-C$_4$ alkoxycarbonyl, benzyl, or benzyl substituted by one or two of the same or different groups selected from C$_1$-C$_4$ alkyl, C$_1$-C$_4$ alkoxy, 3,4-methylenedioxy, halogen or nitro; Z is protected hydroxy; m is 0, 1, or 2; and p is 0 or 1.

2. The compound of claim 11 wherein R" is C$_1$-C$_4$ alkoxycarbonyl.

3. The compound of claim 1 wherein p is 0.

4. The compound of claim 3 wherein m is 1 and R" is methoxycarbonyl.

5. The compound of claim 4 wherein the boron enolate is a di-n-butyl boron enolate.

* * * * *

UNITED STATES PATENT AND TRADEMARK OFFICE
CERTIFICATE OF CORRECTION

PATENT NO. : 4,845,229

DATED : July 4, 1989

INVENTOR(S) : Chi-Nung W. Hsiao and Marvin J. Miller

It is certified that error appears in the above-identified patent and that said Letters Patent is hereby corrected as shown below:

Column 1, line 5, "Seer." should read -- Serial --.

Column 1, line 59, "acetidinone" should read -- azetidinone --.

Column 2, line 40 "with an" should read -- in an --.

Column 3, line 16, "hydroxamate" should read -- hydroxylamine --.

Column 3, line 35, "obtaned" should read -- obtained --.

Column 4, line 33, "development a yellowish" should read -- development of a yellowish --.

Column 4, line 53, "hydroxamate" should read -- hydroxylamine --.

Column 4, line 55, "hydroxamate" should read -- hydroxylamine --.

Column 4, line 61, "hydroxamate" should read -- hydroxylamine --.

Column 4, line 63, "hydroxamates" should read -- hydroxylamines --.

Column 5, line 3, "hydroxamates" should read -- hydroxylamines --.

Column 6, line 43, "kown" should read -- known --.

Column 6, lines 45 through 53

" 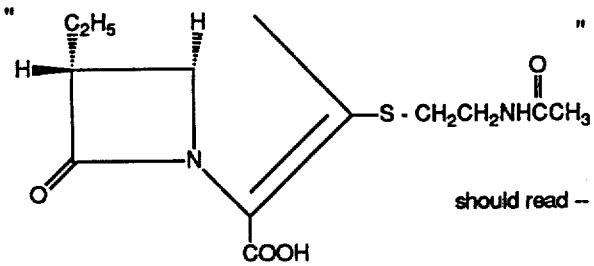 " should read -- 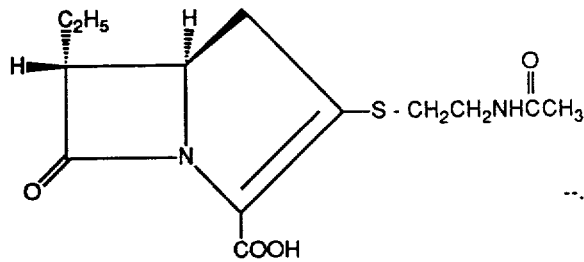 --.

UNITED STATES PATENT AND TRADEMARK OFFICE
CERTIFICATE OF CORRECTION

PATENT NO. : 4,845,229

DATED : July 4, 1989

INVENTOR(S) : Chi-Nung W. Hsiao and Marvin J. Miller

It is certified that error appears in the above-identified patent and that said Letters Patent is hereby corrected as shown below:

Column 6, lines 57 through 65

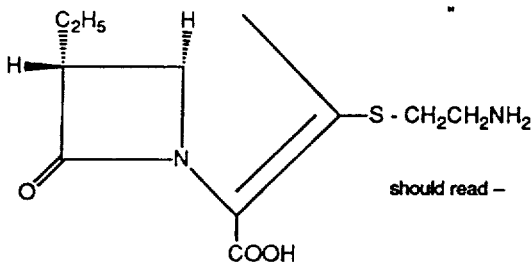 should read — 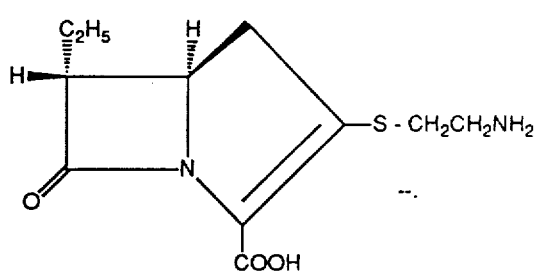 —.

Column 7, line 23, "-methylate" should read — -mesylate —.

Column 8, line 21, "procedure" should read — procedures —.

Column 8, line 56, "aldo" should read — aldol —.

Column 8, line 59, "followin" should read — following —.

Column 10, line 34, "in tri-" should read — and tri- —.

Column 13, line 22, "4.85 (7.25" should read — 4.85 (S, 2H), 7.25 —.

Column 14, line 38, "claim 11" should read — claim 1 —.

Signed and Sealed this

First Day of January, 1991

*Attest:*

HARRY F. MANBECK, JR.

*Attesting Officer*  *Commissioner of Patents and Trademarks*